United States Patent [19]
Frankenreiter et al.

[11] Patent Number: 4,953,557
[45] Date of Patent: Sep. 4, 1990

[54] BLOOD PRESSURE MONITOR

[75] Inventors: Michael Frankenreiter, Sindelfingen; Rainer Rometsch, Wildberg; Jens-Peter Seher, Stuttgart, all of Fed. Rep. of Germany

[73] Assignee: Hewlett-Packard Company, Palo Alto, Calif.

[21] Appl. No.: 345,927

[22] Filed: May 1, 1989

[30] Foreign Application Priority Data

May 14, 1988 [EP] European Pat. Off. ......... 88107800.0

[51] Int. Cl.⁵ .............................................. A61B 5/02
[52] U.S. Cl. ................... 128/677; 128/680; 128/681
[58] Field of Search .................. 128/672, 677–686, 128/687–690

[56] References Cited

U.S. PATENT DOCUMENTS 2,865,365 12/1958 Newland et al. ................ 128/681
4,005,701 2/1977 Aisenberg et al. .............. 128/680
4,658,829 4/1987 Wallace ......................... 128/675 X
4,800,892 1/1989 Perry et al. ..................... 128/677

Primary Examiner—Max Hindenburg
Assistant Examiner—J. P. Lacyk
Attorney, Agent, or Firm—Richard F. Schuette

[57] ABSTRACT

A monitor for the automated non-invasive measurement of a patient's blood pressure comprising apparatus for automatically inflating and deflating a cuff which is to be applied around a patient's extremity, first and second pressure sensors coupled to the airway of said cuff, each providing an electronic signal indicative of cuff pressure, and a processor responding to the signals obtained by said pressure sensors for stopping the inflation of the cuff when a maximum cuff pressure is reached, and for calculating the blood pressure from the oscillations of the pressure signal. A memory is connected to said processor in which calibration values indicating the pressure related to the electronic signals provided by each of said two pressure sensors are stored. The processor is adapted to access and compare those calibration values which correspond to the actual values of said electronic signals provided by said two sensors to monitor supply and/or reference voltages, and to cause the deflation of the cuff when the actual calibration values differ from each other or the supply and/or reference voltages each differ from a related predetermined value more than a predetermined amount, thus preventing any pressure raise over predetermined limits in case of any malfunction of the monitor without the use of mechanical pressure switches.

26 Claims, 1 Drawing Sheet

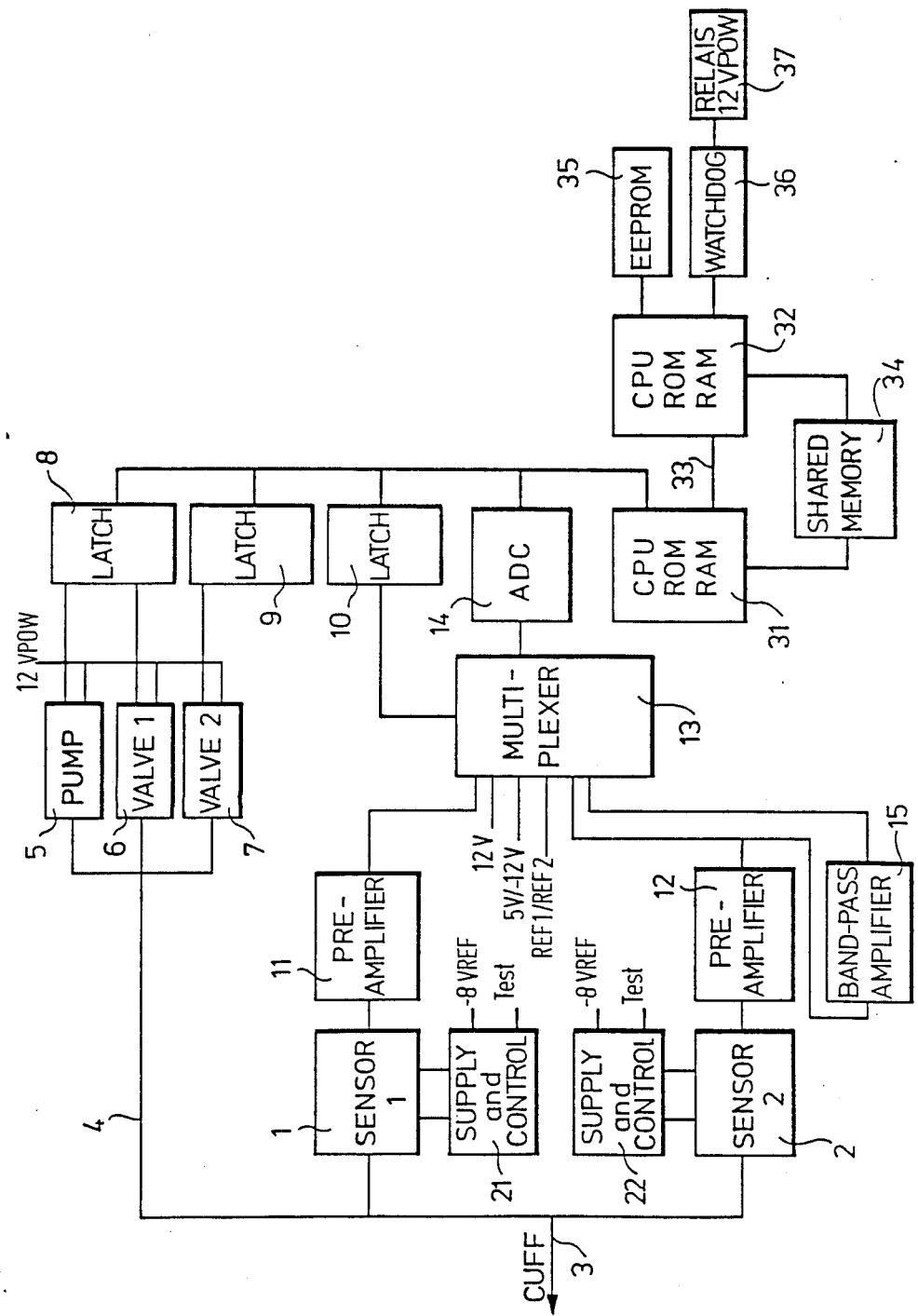

BLOOD PRESSURE MONITOR

BACKGROUND OF THE INVENTION

This invention relates to a monitor for the automated non-invasive measurement of a patient's blood pressure comprising means for automatically inflating and deflating a cuff which is to be applied around a patient's extremity, in particular an arm, first and second pressure sensors coupled to the airway of that cuff, each sensor providing an electronic signal indicative of cuff pressure, and electronic means responding to the signals obtained by said pressure sensors for stopping the inflation of the cuff when a certain predetermined maximum cuff pressure is reached, for calculating the blood pressure, in particular from the pressure signal, and for detecting malfunctions of the pressure sensors.

Such a monitor is described in EP-Application No. 88 102 787.4 and thus is considered to represent the state of the art. However, other than the indication that two independent pressure sensors may be used to control each other in order to detect malfunctions, fact that the fact that sensors are required for monitoring the cuff pressure, in particular the maximum cuff pressure, and the fact that the monitor stops inflating the cuff when the maximum cuff pressure is achieved, the EP-88 102 787.4 does not describe any details of such a monitor.

In a monitor for the automated non-invasive measurement of a patient's blood pressure which includes a cuff as a means for exerting an external counter pressure upon the patient's artery, security means must be provided which prevent the surpassing of predetermined pressure values independently of the operation of blood pressure measurement. Such means must guarantee in case of failure of the electronic pressure sensor, of the inflating means and of the electronic means provided for evaluating the blood pressure, that a pressure can not be exerted which has too high a value or too long a duration and thus could injure the patient. If the same monitor should be appropriate for being used with newborns, children and adults, besides of the evaluation algorithms and, the threshold values of pressure sensors must be adapted to the patient. A proposition of the IEC determines the maximum cuff pressure for newborns at 165 mmHg, for children at 220 mmHg and for adults at 330 mmHg.

In presently available monitors, mechanical pressure switches are used which disconnect the supply voltage from at least relevant parts of the monitor when the maximum pressure is reached. Such a mechanical pressure switch is essentially comprised of an elastic membrane which is moved by the exerted pressure and actuates a micro switch if the exerted pressure surmounts a predetermined value. It suffers from being expensive, bulky, susceptible to shocks, and affected by wide tolerances. Further, since it has an elastic membrane, it is not free of wear. Finally, an essential drawback of such pressure switch consists in that its operation can only be tested when too high a pressure occurs, i.e. in case of a failure, but not during normal operation.

If provision has to be made that short pressure peaks in the system which may be caused by movement artifacts of the patient do not trigger the pressure switch, a certain damping must be provided in the tube system, which damping, however, has the disadvantage to extend the response time of the system.

In order to keep the expenditure low, in most cases only one pressure switch is used which has its threshold value set to the highest value, i.e. the value for adults. If the dependence of the pressure threshold on the patient has to be considered, either a pressure switch having three defined threshold values or three pressure switches having different threshold values are needed. The threshold value assigned to the patient must then be logically or mechanically enabled whereas the two other threshold values are to be disabled.

BRIEF SUMMARY-OF THE PREVENTION

It is therefore a major objective of the present invention to provide a monitor for the automated non-invasive measurement of blood pressure which has the required reliability without making use of mechanical safety pressure switches.

This objective is solved in a monitor of the type described above by the use of failure sensing means included in said electronic means, said failure sensing means comprising means for storing calibration values indicating the pressure related to the electronic signals provided by each of said two pressure sensors, means for accessing and comparing those calibration values which correspond to the actual values of said electronic signals provided by said two sensors, means for monitoring supply and/or reference voltages, and means for causing the deflation of the cuff when the actual calibration values differ from each other or the supply and/or reference voltages differ from a predetermined value more than a predetermined amount.

In this way, the invention provides for a close monitoring of the signals and voltages which are crucial for a safe operation of the monitor. Since the two pressure sensors used in the same monitor may have different characteristics, their calibration values are stored and accessed in response to the electronic signals provided by said sensors in order to determine the pressure measured thereby. If the accessed calibration values indicate that both sensors respond to the same pressure, it may be assumed that both sensors operate correctly. However, even if the accessed calibration values are similar, the indicated pressures may be wrong, and this because of supply voltages and reference voltages may differ from their predetermined values, so that the electronic signals provided by the pressure sensors can be different from those which said sensors would produce in response to the actual pressure if said supply and/or reference voltages were correct. In addition to the comparison between the calibration values accessed in response to the electronic signals provided by the said two sensors, the supervision of supply and/or reference voltages makes sure that the pressure indication is always correct so that it can be relied upon for controlling all functions of the monitor, especially stopping the inflation of the cuff when a certain predetermined maximum cuff pressure is reached. There is no more any need to provide extra mechanical pressure switches for safety reasons.

Through the invention makes sure that the pressure measurement produces correct values as long as the values determined by the two pressure sensors are similar, and as long as the supply and/or reference voltages are correct, and though correct supply and/or reference voltages are also a first condition for a correct operation of the electronic means included in said monitor, there is still the possibility that other components of the monitor are failing and are causing trouble by their failure. Thus, for example, trouble may be caused by a malfunction of the electronic means for calculating the blood pressure and for controlling the automated function of the monitor. In order to obviate severe consequences of such a malfunction, in a preferred embodiment of the invention said electronic means comprises a first processor for calculating the blood pressure and a second processor for controlling the internal and external data transfer. The failure sensing means comprises a shared memory coupled to said two processors and means for causing the deflation of said cuff when the data transfer via said shared memory fails. In this embodiment, the data transfer via said shared memory provides for a continuous check of the operation of said two processors, so that a malfunction of one of these processors also leads to deflation of the cuff and to switching off of the monitor.

The continuous monitoring of said two processors may be further improved by operating the second processor as a master processor with respect to the first processor, and by coupling a watchdog circuit to the second processor, which watchdog circuit causes the deflation of said cuff when it senses a failure of the second processor. A watchdog circuit is common in the microprocessor art and is designed to receive a predetermined control signal within predetermined time intervals from the watched processor and to produce an alarm signal, especially a signal for switching off the monitor from the supply voltage, in case that it does not correctly receive the said control signal.

In order to improve the security also with respect to the means for automatically inflating and deflating the cuff, according to a preferred embodiment of the invention said means includes a pump comprising first electrical drive means, a normally open valve which may be closed by second electrical drive means, and means for disconnecting the supply voltages from that first and second drive means in case of failure, so that the pump immediately ceases operation and the valve adopts its open position which allows air to escape from the cuff and thus the cuff to deflate. Here again, the security may still be improved by connecting a normally closed valve in parallel to the normally open valve, which normally closed valve may be opened by third electrical drive means, so that this valve may be positively opened by applying a supply voltage in case that by some failure the opening of the first valve is barred.

It is an essential advantage of the supervision achieved for the different portions of the electronic means that there is no need to provide for each pressure sensor its own separate signal channel but that the two pressure sensors may be connected to a single supervising circuitry. Thus, in a preferred embodiment of the invention, the electronic means comprise a multiplexer having inputs to which the electronic signals provided by said two sensors and said supply and/or reference voltages are connected, whereas the output of the multiplexer is connected to an analog/digital-converter having an output to which the electronic means is connected. Finally, said failure sensing means may comprise means for producing test signals and means for monitoring the response of said sensors and/or of said electronic means to said test signals, which monitoring means effects the deflation of said cuff when the sensed response is outside of predetermined limits.

BRIEF DESCRIPTION OF THE DRAWINGS

The single drawing is a block diagram illustrating the components of the invention.

A monitor embodying the invention will now be described—by way of non-limiting example—with reference to the accompanying drawing which shows the block diagram of such a monitor.

The monitor having the circuit diagram shown in the drawing, comprises two sensors 1 and 2 which are connected symmetrically to a connection line 3 leading to a cuff (not shown). To the connection line 3 are further connected by means of tube 4 a pump 5, a first valve 6, and a second valve 7. The pump 5 and the valves 6, 7 are each provided with its own drive means (not shown). They are connected in parallel. Pump 5 and first valve 6 are connected to a common first latch 8, whereas valve 7 is connected to a second latch 9.

The first and second sensors 1, 2 are each connected via a pre-amplifier 11, 12 to a multiplexer 13 which has its output coupled to the input of an A/D-converter 14. Further, the output of the second pre-amplifier 12 is connected via a band-pass amplifier 15 to another input of multiplexer 13. The pressure sensors 1 and 2 are piezoelectric sensors, each one being connected to a supply and control unit 21 22, respectively, each supply and control unit having inputs for reference and test signals.

The output of the A/D-converter 14 is coupled to a first processor 31 which cooperates with a second processor 32. Both processors have their own memories (ROM, RAM). They are coupled by a control line 33 and by a shared memory 34. Further, to the second processor 32 an EEPROM and a watchdog circuit 36 are coupled, the watchdog circuit controlling a power relay 37. Finally, a third latch 10 is connected between the output of the A/D-converter 14 and multiplexer 13.

In operation, under the control of the first processor 31, input signals of the multiplexer 13, to the first processor 31. This first processor is arranged to perform the calculations which are necessary to derive the values of the systolic, diastolic and mean blood pressure from the oscillations of the pressure signal provided by the pressure sensors and especially by the second pressure sensor 2 via band-pass amplifier 15. The second processor 32 is arranged to control the internal and external data transfer, including the operation of the first processor 31, so that the second processor 32 operates as a master processor with respect to the first processor 31.

Before its first use, the monitor is initiated by inflating the cuff to predetermined pressure values which may be determined by means of separate precision instruments. These pressure values are put into EEPROM 35 together with digital signals derived from the outputs of pre-amplifiers 11 and 12 and connected by means of multiplexer 13 to EEPROM 35 via A/D-converter 14, first processor 31, shared memory 34 and second processor 32. In this way, in EEPROM 35 calibration values are stored which indicate the pressure related to the electronic signals provided by each of said two pressure sensors 1 and 2 via pre-amplifiers 11 and 12, respectively.

When, after this initiation step, for measuring blood pressure the cuff is inflated by activating the drive means of pump 5, the output signals of first and second sensors 1 and 2 indicate the increasing pressure. As long as the pressure values retrieved from EEPROM 35 in response to the electronic signals provided by said sensors are equal or do not differ more than a predetermined amount, the two sensors are certainly correctly functioning so that the measurement may be continued.

If, however, a pressure difference occurs which surmounts the predetermined amount, this difference indicates that at least one of the sensors 1 and 2 or one of the associated preamplifiers 11, 12 is defective so that a malfunction might occur. In this case, the first processor 31 which performs the comparison, releases latch 8 so that the drive means of pump 5 and of valve 6 are disconnected from their 12 V power supply. First valve 6 being arranged to being normally open, thus opens by itself when the power supply is disconnected, whereas pump 5 stops. The stopping of pump 5 and the opening of valve 6 results in deflating the cuff so that any danger of injuring the patient by providing a too high pressure in said cuff is removed.

This reciprocal control of sensors 1 and 2 does not prevent damages which are caused by a malfunction of the circuitry following multiplexer 13 or by defects which have the result that sensors 1 and 2 provide signals which are equal but wrong. The second case may happen if the supply and reference voltages controlling the operation of the sensors are different from and especially lower than predetermined values. In this case, the electronic signals provided by sensors 1 and 2 are equal but have both a value which is lower than that corresponding to the actual pressure. Thus, by monitoring these electronic signals, the danger exists that the cuff is inflated to a pressure which is higher than the predetermined maximum pressure and which could injure the monitored patient. In order to obviate this danger, supply, reference and control voltages are connected by multiplexer 13 to processors 31 and 32 wherein these voltages are checked. Here again, the deflation of the cuff is induced by activating latch 8 and thus cutting the power from pump 5 and valve 6 if any one of the supply, reference or control voltages have not the correct value.

It should be mentioned that by storing the calibration values in the EEPROM 35 connected to the second processor 32, the characteristic of the power channel between the sensors and the EEPROM is reflected in the calibration values stored therein. Further, controlling the supply and reference voltages by the first processor 31 also controls the operation of multiplexer 13 and A/D-converter 14.

There is still a need for watching the operation of said two processors 31 and 32. The function of second processor 32 is watched by the watchdog circuit 36 which is arranged to receive from second processor 32 a predetermined code word in predetermined time intervals. If the watchdog circuit 36 does not receive the correct code word in time because of a malfunction of second processor 32, it does activate relay 37 which then cuts the power from the whole monitor, so that again pump 5 is stopped and valve 6 is opened so that a deflation of the cuff occurs. In an analogous way, first processor 31 is watched by means of the shared memory 34. All data exchange between the two processors 31 and 32 occurs via shared memory 34 accompanied by a specific modification of the transferred data. If the second processor recognizes that the transferred data are not correctly modified, the second processor 32 again recognizes a failure and stops transmitting code words to the watchdog circuit 36. Thus, watchdog circuit 36 again responds and disconnects the power supply by means of relay 37, thereby effecting the stopping of pump 5 and the opening of valve 6. It should be mentioned that line 33 connecting the two processors 31 and 32 is not used for a data transfer but for the passing of control signals only, especially of enabling and synchronizing signals.

Second valve 7 is different from first valve 6 in that it is normally closed and may be opened by connecting power thereto. This power may be connected by means of latch 9. The reason is that in case of a mechanical defect which prevents first valve 6 to return into its open position when the power supply is disconnected, valve 2 may be positively opened by connecting power to it. Thus, second valve 7 is another means for rendering the operation of the described monitor as safe as possible.

Finally, in the disclosed embodiment means are provided to connect test signals to the sensors 1 and 2 via supply and control circuits 21 and 22, respectively. The response of said sensors and of the electronic components connected thereto to these test signals is monitored by said processors, and here again the operation of the monitor is stopped and, if necessary, a deflation of the cuff effected when the monitoring of the response to the test signals indicates a malfunction of the monitor.

It will be apparent that the embodiment of the invention as described and illustrated is only exemplary and that various modifications can be made within the scope of the invention as defined in the appended claims. For example, EEPROM 35 may include a plurality of blocks, each block containing all calibration values for the same pressure range, which calibration values have been stored successively. When checking the pressure sensors, the calibration values of all blocks are read and a failure is indicated if a predetermined number of said values is not comprised within predetermined limits. Further, when a failure is detected, in addition to deflating the cuff an optical and/or acoustical alarm signal may be produced.

We claim:

1. Apparatus for automated measurement of blood pressure by application of air pressure to a cuff in such a manner as to prevent a harmful pressure from occurring in said cuff comprising
   air control means including a pump for inflating or deflating a cuff via an outlet,
   first and second pressure sensors adapted to be coupled to a cuff so as to respectively provide first and second signals indicative of the pressure in the cuff,
   means having stored calibration data for each of said pressure sensors,
   electronic means for activating said pump, for determining from said first and second signals and said calibration data the calibrated values of pressure for each of said sensors and for causing said air control means to deflate a cuff if either of said calibrated values exceeds a predetermined amount, and
   said electronic means having means for comparing said calibrated pressure values and for causing said air control means to deflate a cuff when they differ by more than a predetermined amount.

2. Apparatus as set forth in claim 1 wherein said sensors operate in response to supply and reference voltages and wherein said electronic means causes said air control means to deflate a cuff if either of these voltages differ from respective given values by more than a predetermined amount.

3. Apparatus as set forth in claim 2 where in said electronic means is comprised of:
   a first processor means for calculating blood pressure, a second processor means for controlling internal and external data transfer, a shared memory coupled to said first and second processor means, and means for causing said air control means to deflate a cuff when there is a failure of data transfer in said shared memory indicating a failure in said first processor means.

4. Apparatus as set forth in claim 3 wherein said second processor means operates as a master processor for said first processor means and further comprising:

a watchdog circuit coupled to said second processor means, having means for causing said air control means to deflate a cuff whenever it senses a failure in said second processor means.

5. Apparatus as set forth in claim 4 wherein said air control means includes:

a normally open valve coupled between said outlet of said pump and ambient air, and means for closing said valve when said pump is activated and for permitting said valve to return to its normally open position when said pump is disabled.

6. Apparatus as set forth in claim 4 further comprising:

a normally closed valve coupled between said outlet of said pump and ambient air, and means for opening said normally closed valve when said pump is disabled.

7. Apparatus as set forth in claim 2 wherein said air control means includes:

a normally open valve coupled between said outlet of said pump and ambient air, and means for closing said valve where said pump is activated and for permitting said valve to return to its normally open position when said pump is disabled.

8. Apparatus as set forth in claim 2 further comprising:

a normally closed valve coupled between said outlet of said pump and ambient air, and means for opening said normally closed valve when said pump is disabled.

9. Apparatus as set forth in claim 3 wherein said air control means includes:

a normally open valve coupled between said outlet of said pump and ambient air, and means for closing said valve when said pump is activated and for permitting said valve to return to its normally open position when said pump is disabled.

10. Apparatus as set forth in claim 3 further comprising:

a normally closed valve coupled between said outlet of said pump and ambient air, and means for opening said normally closed valve when said pump is disabled.

11. Apparatus as set forth in claim 1 wherein said electronic means is comprised of:

a first processor means for calculating blood pressure, a second processor means for controlling internal and external data transfer, a shared memory coupled to said first and second processor means, and means for causing said air control means to deflate a cuff when there is a failure of data transfer in said shared memory indicating a failure in said first processor means.

12. Apparatus as set forth in claim 11 wherein said second processor means operates as a master processor for said first processor means and further comprising:

a watchdog circuit coupled to said second processor means having means for causing said air control means to deflate a cuff whenever it senses a failure in said second processor means.

13. Apparatus as set forth in claim 12 wherein said air control means includes:

a normally open valve coupled between said outlet of said pump and ambient air, and means for closing said valve when said pump is activated and for permitting said valve to return to its normally open position when said pump is disabled.

14. Apparatus as set forth in claim 12 further comprising:

a normally closed valve coupled between said outlet of said pump and ambient air, and means for opening said normally closed valve when said pump is disabled.

15. Apparatus as set forth in claim 11 further comprising:

a normally closed valve coupled between said outlet of said pump and ambient air, and means for opening said normally closed valve when said pump is disabled.

16. Apparatus as set forth in claim 11 wherein said air control means includes:

a normally open valve coupled between said outlet of said pump and ambient air, and means for closing said valve where said pump is activated and for permitting said valve to return to its normally open position when said pump is disabled.

17. Apparatus as set forth in claim 1 wherein said air control means includes:

a normally open valve coupled between said outlet of said pump and ambient air, and means for closing said valve where said pump is activated and for permitting said valve to return to its normally open position when said pump is disabled.

18. Apparatus as set forth in claim 1 further comprising:

a normally closed valve coupled between said outlet of said pump and ambient air, and means for opening said normally closed valve when said pump is disabled.

19. Apparatus as set forth in claim 1 further comprising:

means for providing test signals to said first and second sensors, means for monitoring the responses to said test signals, and means for causing said air control means to deflate a cuff if the response differs from what is expected by more than a predetermined limit.

20. Apparatus for non invasively monitoring the blood pressure of a patient comprising:

a cuff, means for inflating and deflating said cuff, first and second pressure sensors coupled to said cuff for providing separate signals representing the pressure in said cuff, means for monitoring said signals so as to calculate the blood pressure respectively indicated thereby and for deflating said cuff when said signals indicate a pressure that exceeds a predetermined maximum or when said signals produced in response to test pressure in said cuff represent pressures that differ by more than a predetermined amount.

21. Apparatus for automated measurement of blood pressure by application of air pressure to a cuff in such manner as to prevent a harmful pressure from occurring in said cuff comprising:

air control means including a pump for inflating or deflating a cuff via an outlet, first and second pressure sensors adapted to be coupled to a cuff so as to respectively provide first and second signals indicative of the pressure in the cuff, means having stored calibration data for each of said pressure sensors, a first processor means for activating said pump, for determining from said first and second signals and said calibration data the calibrated values of pressure for each of said sensors, for causing said air control means to deflate a cuff if either of said calibrated values exceeds a predetermined amount, for comparing said calibrated pressures and for causing said air control means to deflate a cuff when they differ by more than a predetermined amount, a second processor means for controlling internal and external data transfer of said first processor means, a shared memory coupled to said first and second processor means, and means for causing said air control means to deflate a cuff when there is a failure of data transfer in said shared memory indicating a failure in said first processor.

22. Apparatus as set forth in claim 21 wherein said sensors operate in response to supply and reference voltages and wherein said first processor means causes said air control means to deflate a cuff if either of these voltages differ from respective given values by more than predetermined amounts.

23. Apparatus as set forth in claim 21 wherein said second processor means operates as a master processor means for said first processor means and further comprising:

a watchdog circuit coupled to said second processor means having means for causing said air control means to deflate a cuff whenever it senses a failure in said second processor means.

24. Apparatus as set forth in claim 23 wherein said air control means includes:

a normally open valve coupled between said outlet of said pump and ambient air, and means for closing said valve when said pump is activated and for permitting said valve to return to its normally open position when said pump is disabled.

25. Apparatus for automated measurement of blood pressure by application of air pressure to a cuff in such manner as to reduce the chance of harmful pressure appearing in said cuff comprising:

air supply means for controllably supplying inflation and deflation air pressures for a blood pressure cuff, first and second pressure sensors adapted to be coupled to a blood pressure cuff for providing first and second signals in response to pressure therein, means for supplying operating and reference voltages to said sensors, and means including a first processor for monitoring said signals and said voltages and for causing said air supply means to supply a deflation pressure if (a) the pressure represented by either of said first and second signals exceeds a given maximum (b) the difference between the pressures represented by said first and second signals exceeds a given amount and (c) the difference between any of said operating and reference voltages and given respective values exceeds given respective amounts.

26. Apparatus as set forth in claim 25 further comprising:

a master processor coupled to said first processor via a control line and a shared memory, a watchdog circuit coupled to said master processor, and means coupled to said watchdog circuit for controlling said air supply means, whereby said air supply means provides a deflation air pressure if either said first processor or said master processor malfunctions.

* * * * *